(12) United States Patent
Persson et al.

(10) Patent No.: US 11,633,303 B2
(45) Date of Patent: Apr. 25, 2023

(54) SMART EARMUFF AND METHOD FOR IMPROVED USE OF AN EARMUFF

(71) Applicant: HUSQVARNA AB, Huskvarna (SE)

(72) Inventors: Alexander Persson, Tenhult (SE); Cornelia Gustafsson, Jönköping (SE)

(73) Assignee: HUSQVARNA AB, Huskvarna (SE)

( * ) Notice: Subject to any disclaimer, the term of this patent is extended or adjusted under 35 U.S.C. 154(b) by 1245 days.

(21) Appl. No.: 16/089,661

(22) PCT Filed: Mar. 28, 2017

(86) PCT No.: PCT/EP2017/057265
§ 371 (c)(1),
(2) Date: Sep. 28, 2018

(87) PCT Pub. No.: WO2017/167722
PCT Pub. Date: Oct. 5, 2017

(65) Prior Publication Data
US 2019/0110929 A1 Apr. 18, 2019

(30) Foreign Application Priority Data

Mar. 31, 2016 (SE) .................................. 1650419-3

(51) Int. Cl.
*H04R 25/00* (2006.01)
*A61F 11/14* (2006.01)
*H04R 1/10* (2006.01)

(52) U.S. Cl.
CPC .............. *A61F 11/14* (2013.01); *H04R 1/10* (2013.01); *H04R 1/1041* (2013.01);
(Continued)

(58) Field of Classification Search
CPC .............. A61F 11/14; A61F 2250/0075; A61F 2250/0012; A61F 11/145; H04R 1/10; H04R 1/1041
See application file for complete search history.

(56) References Cited

U.S. PATENT DOCUMENTS

| | | | |
|---|---|---|---|
| 3,938,614 A | 2/1976 | Ahs | |
| 5,920,911 A | 7/1999 | Cushman | |
| 8,243,946 B2 * | 8/2012 | Burge | H04R 1/1041 381/74 |

FOREIGN PATENT DOCUMENTS

| | | |
|---|---|---|
| DE | 203 11 724 U1 | 12/2004 |
| DE | 20 2011 110 400 U1 | 12/2013 |

(Continued)

OTHER PUBLICATIONS

Berger, E., "Tips for Fitting Hearing Protectors," E•A•RLOG® 19, E•A•RLOG® is a registered trademark of Aearo Company. Copyright 1996. First printing 1988, pp. 1-4.

(Continued)

*Primary Examiner* — Phylesha Dabney
(74) *Attorney, Agent, or Firm* — Burr & Forman LLP (57) ABSTRACT

An acoustic earmuff device comprising a pair of earmuff cup assemblies such that each is configured to be arranged at a location proximate to an ear of an user, wherein each earmuff cup assembly comprises means (320) for adapting a pressure applied to the location proximate to the ear so that the pressure around the ear is evenly distributed and a even seal is achieved, wherein the means for adapting a pressure comprises an adaptive layer (324) that is configured to apply the pressure around the ear evenly regardless whether that location comprises any protruding element (2).

14 Claims, 7 Drawing Sheets

(52) U.S. Cl.
CPC ..... *A61F 11/145* (2022.01); *A61F 2210/0076* (2013.01); *A61F 2250/0004* (2013.01); *A61F 2250/008* (2013.01); *A61F 2250/0009* (2013.01); *A61F 2250/0012* (2013.01); *A61F 2250/0075* (2013.01)

(56) References Cited

FOREIGN PATENT DOCUMENTS

| EP | 0 967 592 A2 | 12/1999 |
| EP | 2 238 951 A1 | 10/2010 |
| GB | 791660 A | 3/1958 |
| WO | 2009/018677 A1 | 2/2009 |
| WO | 2015/179975 A1 | 12/2015 |

OTHER PUBLICATIONS

Gerges, S.N.Y. et al., "Earmuff Comfort," Proceedings of 20th International Congress on Acoustics, ICA 2010, Aug. 23-27, 2010, Sydney, Australia, pp. 1-4.

Nixon, C.W. and Knoblach W.C., "Hearing Protection of Earmuffs Worn Over Eyeglasses," AD-785 386, Aerospace Medical Research Laboratory, Wright-Patterson Air Force Base, Ohio, Jun. 1974, pp. 1-32.

International Search Report and Written Opinion for International Application No. PCT/EP2017/057265 dated Sep. 13, 2017.

International Preliminary Report on Patentability for International Application No. PCT/EP2017/057265 dated Oct. 2, 2018.

\* cited by examiner

SMART EARMUFF AND METHOD FOR IMPROVED USE OF AN EARMUFF

TECHNICAL FIELD

This application relates to a smart earmuff and in particular to an earmuff that provides an improved hearing protection for a user. The teachings herein primarily relates to earmuffs for use in environments with loud noises.

BACKGROUND

Earmuffs are important protective equipment in order to prevent loss of or reduction of hearing resulting from extended exposures to loud noises, such that may be encountered in industrial environments for example in foresting. Other uses for noise excluding hearing protectors include reducing a sound level for study, sleep, or audio purposes. Earplugs could also be used for noise exclusion, although earmuffs tend to deliver higher noise protection as well as being more practical to use, being easier to remove and don repeatedly as is common in work environments. An earmuff device further has the benefit of having a warming effect when used outdoors in cool weather.

In order for the earmuff to efficiently reduce noise to a level which is below a certain limit, such as set by a safety standard, it is crucial that the earmuff has a great fit for the user to ensure an even seal between the ear and the earmuff. However, in prior art solutions this is not always the case. A large variety of users may use the same earmuff which may or may not use glasses, hearing aids or earplugs underneath the earmuff. These obstacles may cause a bad fit. Furthermore, the shape of the users head may also cause an uneven seal of the earmuff to the user.

There is thus a need for an improved earmuff which has a great fit for different users regardless of any object the user may be wearing or any shape of the user's head.

SUMMARY

It is an object of the teachings of this application to overcome the problems listed above by providing an acoustic earmuff device comprising a pair of earmuff cup assemblies such that each is configured to be arranged at a location proximate to an ear of a user, wherein each earmuff cup assembly comprises means for adapting a pressure applied to the location proximate the ear so that the pressure around the ear is evenly distributed and an even seal is thereby achieved. The means for adapting a pressure comprises an adaptive layer that is configured to apply the pressure around the ear evenly regardless whether that location comprises any protruding element. The pressure around the ear is evenly distributed regardless if that location comprises any protruding element(s).

The means for applying pressure may comprise a sound-absorbing layer and an adaptive layer. The sound-absorbing layer may comprise a sound-absorbing material and the adaptive layer is formed so that it adapts its shape depending on the location proximate the ear.

The sound-absorbing layer may be arranged adjacent to the adaptive layer and wherein the adaptive layer is arranged to abut the location proximate a users ear when being worn in use.

In one embodiment the acoustic earmuff device further comprises a controller and where the adaptive layer comprises actuation means and means for detecting pressure, said controller is configured to receive a detection signal from the means for detecting pressure that an uneven pressure is detected in an area and transmit an activation signal to the actuation means so that the cylinders in that area will retract.

In one embodiment the means for detecting pressure is a pressure sensor.

In one embodiment the acoustic earmuff device further comprises a controller and a user interface, wherein the controller detects if the user is wearing both earmuff cup assemblies, and if not sends a signal to the user interface which produces a signal detectable by the user.

In one embodiment the acoustic earmuff device further comprises a controller and communication interface, wherein the controller detects if the user is wearing both earmuff cup assemblies, and if not sends a signal to the communication interface which produces a wireless alert signal to nearby operators. This informs nearby operator(s) that one of their colleagues are in the risk of getting hearing damages, which may result in that the operator(s) stops working for a while.

In one embodiment the acoustic earmuff device further comprises a controller and communication interface, wherein the controller detects if the user is wearing both earmuff cup assemblies, and if not sends a signal to the communication interface which transmits a deactivation signal to a power tool, so as to put the power tool into idle mode. This will further increase the protection against high dangerous noises, since the power tool will be switch into idle mode as soon as the user is not wearing the earmuffs correctly.

It is also an object of the teachings of this application to overcome the problems listed above by providing a method for safe use of an acoustic earmuff device according to the teachings herein. The method comprises adaptation of the means for applying pressure so that the pressure around the ear is evenly distributed and an even seal is achieved.

In one embodiment the acoustic earmuff device further comprises a controller and where the adaptive layer comprises actuation means and means for detecting pressure. The method further comprises receiving a detection signal from said means for detecting pressure that an uneven pressure is detected in an area and transmitting an activation signal to the actuation means so that the cylinders in that area will retract.

The inventors of the present invention have realized, after inventive and insightful reasoning that by adapting the pressure of the earmuff cup assemblies, a more even seal between the earmuff and the ear of the user can be achieved.

One benefit is that the earmuff device will have an increased sound protection due to the more even seal. A further benefit lies in that the earmuff device will be even more comfortable to wear.

Other aspects are defined by the appended patent claims and are further explained in the detailed description section as well as in the drawings.

Other features and advantages of the disclosed embodiments will appear from the following detailed disclosure, from the attached dependent claims as well as from the drawings. Generally, all terms used in the claims are to be interpreted according to their ordinary meaning in the technical field, unless explicitly defined otherwise herein. All references to "a/an/the [element, device, component, means, step, etc]" are to be interpreted openly as referring to at least one instance of the element, device, component, means, step, etc., unless explicitly stated otherwise. The steps of any method disclosed herein do not have to be performed in the exact order disclosed, unless explicitly stated.

BRIEF DESCRIPTION OF DRAWINGS

The invention will be described in further detail under reference to the accompanying drawings in which.

DETAILED DESCRIPTION

The disclosed embodiments will now be described more fully hereinafter with reference to the accompanying drawings, in which certain embodiments of the invention are shown. This invention may, however, be embodied in many different forms and should not be construed as limited to the embodiments set forth herein; rather, these embodiments are provided by way of example so that this disclosure will be thorough and complete, and will fully convey the scope of the invention to those skilled in the art. Like numbers refer to like elements throughout.

Figure 1A:
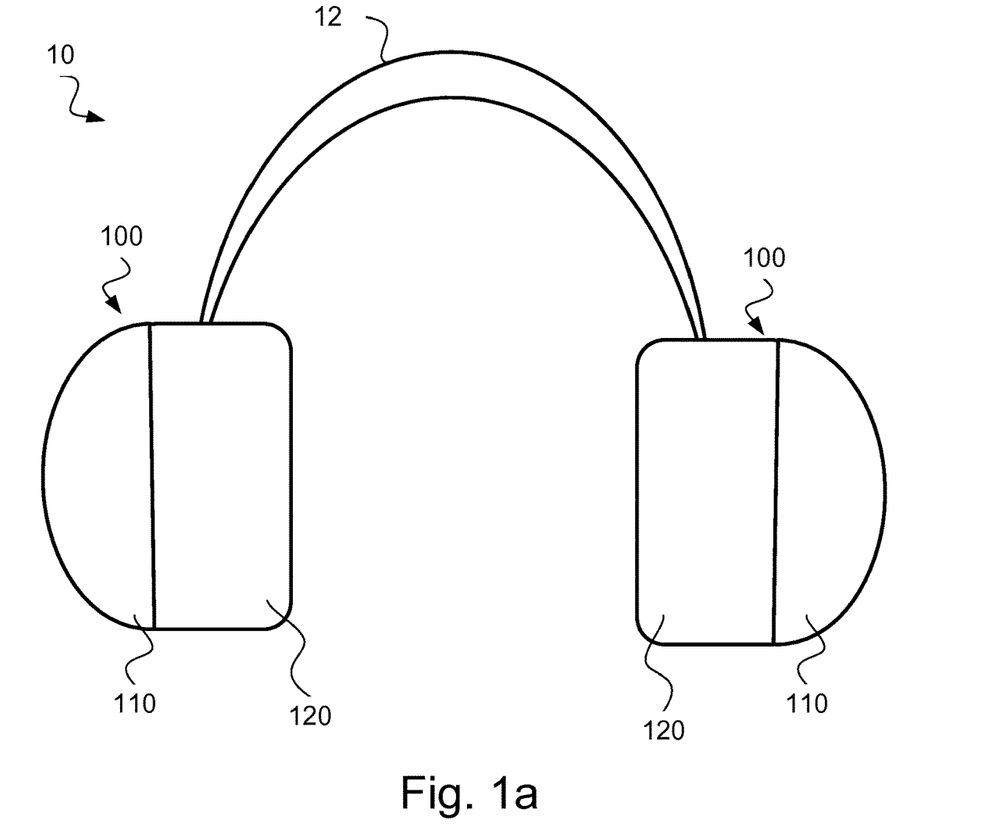
FIGS. 1a-b each shows a schematic view of an earmuff device and earmuff cup assemblies according to one embodiment of the teachings of this application and FIGS. 1c-d each shows a schematic view of a user and a user wearing an earmuff device as seen in FIGS. 1a-b.
Figure 1B:
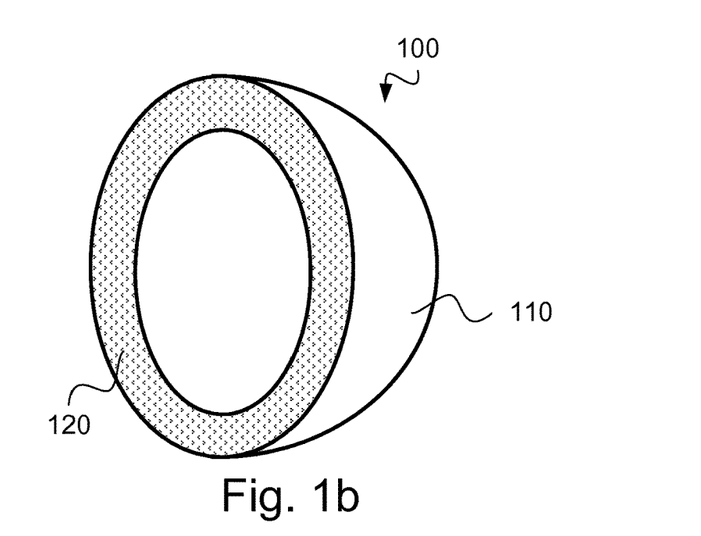

FIGS. 1a and 1b each shows an embodiment of an acoustic earmuff device 10. The earmuff device 10 comprises a generally U-shaped means 12 adapted to be worn around the top of the head of a user. The U-shaped means may be an adjustable headband 12. The headband 12 may comprise a resilient band or a strip made of plastic or rubber having adjustable buckles or other adjustable means. When applied to the head of the user 1, the headband 12 applies pressure on both sides of the head in order to ensure a secure fit. The headband may have an inner surface, facing the head, which is covered in a soft cushion material.

Furthermore, the earmuff device 10 comprises a pair of earmuff cup assemblies 100 connected to the headband 12. Each of the earmuff cup assemblies 100 comprises a rigid cup 110 and means for applying pressure 120. The earmuff cup assembly 100 is at least partly hollow in order to fit around an ear. The earmuff cup assemblies are such that each is configured to be arranged at a location proximate to an ear 4 of a user 1, as seen in FIGS. 1c and 1d.

Figure 1C:
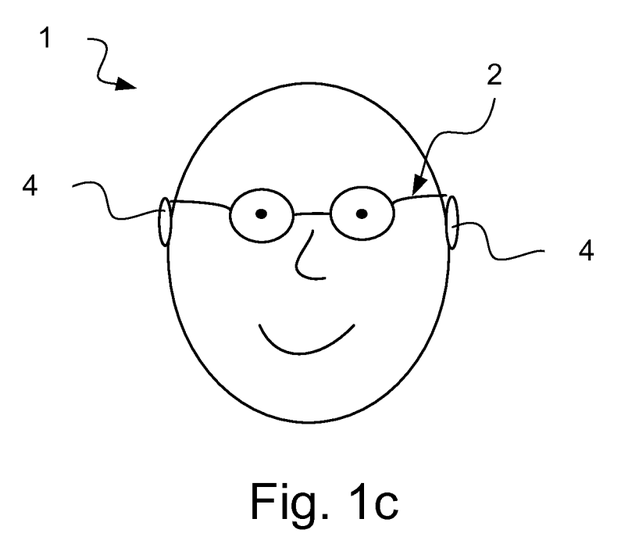
Figure 1D:
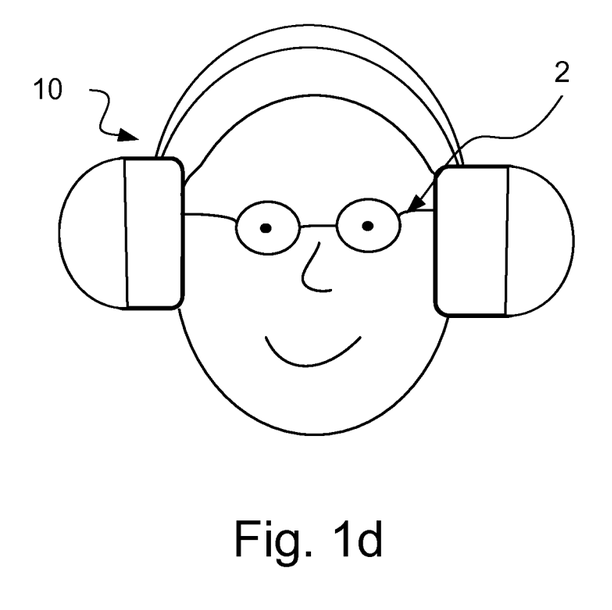

FIG. 1c shows an exemplified user 1, having glasses 2 resting on each ear 4 of the user. In FIG. 1d, the user 1 is wearing an earmuff device 10 which, although glasses 2 are present, creates an even seal around the location proximate to the ears 4.

It should be noted that even though the description herein will focus on passive earmuff devices 10, the teachings herein may also be applied to earmuff devices having active noise cancellation. If the earmuff device 10 uses active noise cancelling methods, the earmuff devices 10 further comprises a microphone, a controller, internal speaker, and a power source such as batteries. In an active earmuff device the microphone listens to the ambient noise, the controller processes the signal and sends out an opposite signal through the speaker. Hence, the unwanted noise is reduced in the ears 4 of the user 1. The term earmuff device should also be seen to also incorporate any type of headset known in the art.

Although not shown in FIG. 1, the acoustic earmuff device 10 may further comprise an audio input, a battery, an on/off switch and/or a power indicator.

If the user 1 is wearing glasses 2, hearing aids or other protruding elements 2 that is at least partially covered or overlapped by the earmuff (as further shown in FIG. 2b), the pressure applied by the earmuff around the ear of the user 1 would be unevenly distributed in prior art earmuff devices. The means for applying pressure 120 is configured to automatically adapt the applied pressure in a location proximate to the ear 4 of the user 1. The pressure around the ear 4 of the user 1 will thus always be evenly distributed, which in turn provides a higher degree of hearing protection as well as a more comfortable working environment.

With an evenly distributed pressure the earmuff cup assemblies 100 will be evenly pressed against the head of the user 1 to provide an even acoustic seal. Different embodiments of means for applying pressure 120 will now be described.

Figure 2A:
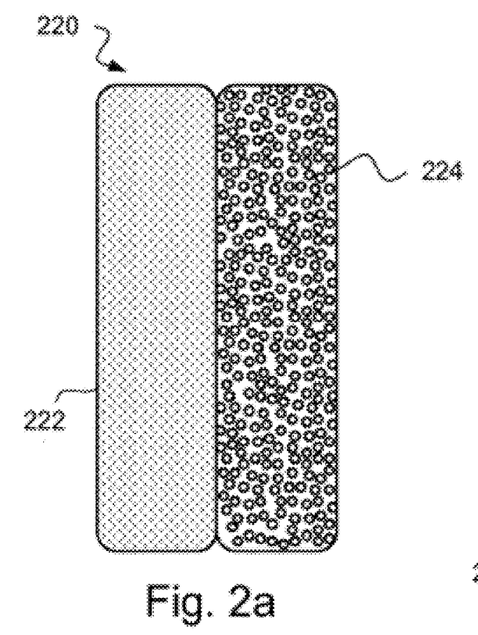
FIGS. 2a-b each shows means for applying pressure in an earmuff cup assembly according to one embodiment of the teachings of this application.
Figure 2B:
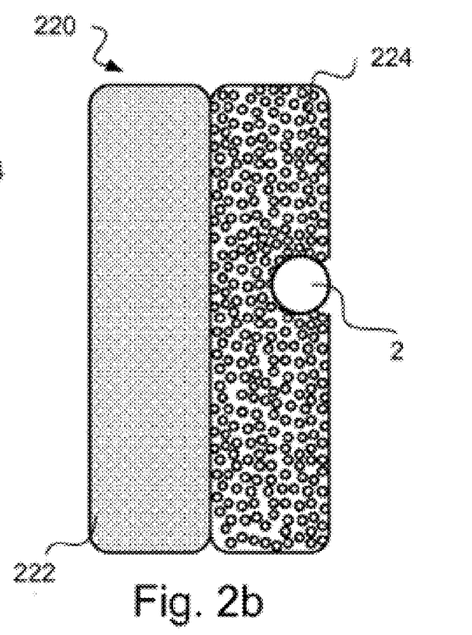

In one embodiment, as seen in FIGS. 2a-b the means for applying pressure 220 comprises two layers; a sound absorbing layer 222 and an adaptive layer 224. The two layers have a shape such that it generally fits the earmuff cup 110. However, the shape of the layers may be any shape, such as cylindrical, round, rectangular and/or irregular.

The sound absorbing layer 222 comprises a sound-absorbing material and may be in the shape of a cushion. The sound-absorbing material may for example be foam or an nonwoven material such as a nonwoven fabric. Nonwoven fabric is a fabric-like material made from long fibers, bonded together by chemical, mechanical, heat or solvent treatment. The term is used to denote fabrics, such as felt, which are neither woven nor knitted. Nonwovens are engineered solutions made of a variety of materials including fibers, powders, particles, adhesives, films and other similar materials. In one embodiment the material making up the sheet may comprise natural fibers, polyester fibers, glass fibers, recycled textile fibers, bicomponent fibers, mineral wool, plastic foam, flame retardant fibers or the like.

In one embodiment the sound absorbing layer 222 comprises a plurality of high-density foams, wherein at least some of the foams are formed by trapping pockets of gas in a liquid or solid state. The sound absorbing layer 222 may also comprise a plurality of thin sheets of flexible polyvinyl chloride or polyurethane, where one of the sheets is vacuum formed filled with foam and/or liquid.

The adaptive layer 224 is arranged to adapt its shape depending on the applied pressure. For example, when a user 1 is putting on an earmuff device 10 for example over a pair of glasses 2 it would lead to that the pressure on the temple of the glasses would increase. The adaptive layer 224 is configured to adapt so that the pressure around the glasses will decrease leading to that the pressure is evenly distributed along the adaptive layer 224, as is seen in FIG. 2b. As the adaptive layer 224 is arranged close to the ear 4 of the user 1, it is beneficial if the material making up the layer is comfortable for the user 1.

As the inventors realized, the idea of the adaptive layer 224 may be regarded as being similar to the idea of a beanbag, which is a sealed bag containing small items which moves around in the bag so to adapt its shape depending on the applied pressure. The adaptive layer 224 may comprise a plurality of small items such as PVC pellets, expanded polystyrene or expanded polypropylene. However, any small items which are easily movable may be used.

In another embodiment, the adaptive layer 224 comprises enclosed liquid. Liquid is an adaptive material which moves around in the enclosure of the adaptive layer 224 when an external pressure, such as from a pair of glasses, is applied. To prevent the liquid from simply changing the shape of the adaptive layer when under the influence of gravity, the liquid is preferably a thick, slow moving viscid liquid and that adaptive layer is relatively thin so as to avoid a drop shaped form of the adaptive layer. The exact thickness of the adaptive layer is related to the density of the liquid.

In one embodiment, the adaptive layer comprises a gas which is under pressure, for example 1.1-1.3 bars. Gases have similar properties to liquid when it comes to distributing pressure, but is also less affected by gravity and so would avoid the drop shaped form of the adaptive layer.

In the embodiment shown in FIGS. 2a-b the adaptive layer 224 is arranged close to the ear, whereas the sound absorbing layer 222 is arranged close to the earmuff cup 110. However, it should be noted that in other embodiments the arrangement could be the opposite, i.e. the sound absorbing layer 222 is arranged close to the ear, whereas the adaptive layer 224 is arranged close to the earmuff cup 110.

It should be understood that although the adaptive layer 224 is not referred to as being sound absorbing, the adaptive layer 224 may still have sound absorbing or noise-reducing properties. If the adaptive layer 224 has satisfying sound-absorbing properties, the means for applying pressure 220 may comprise only one layer, i.e. the adaptive layer 224. That is, the sound absorbing layer and the adaptive layer are one and the same layer.

Figure 3A:
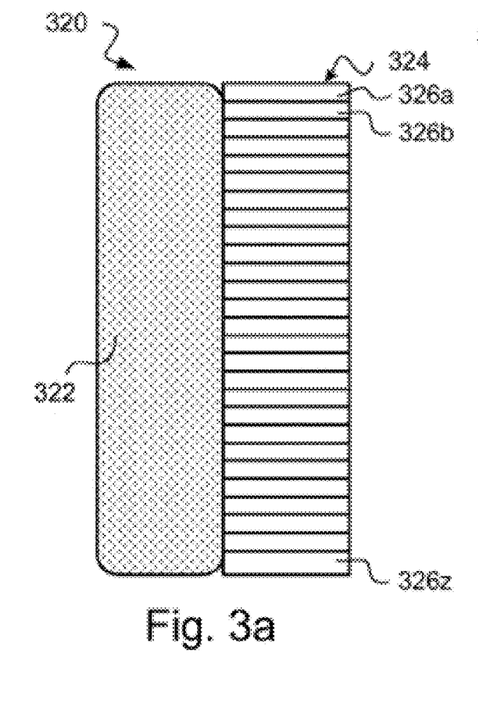
FIGS. 3a-b each shows means for applying pressure in an earmuff cup assembly according to one embodiment of the teachings of this application.
Figure 3B:
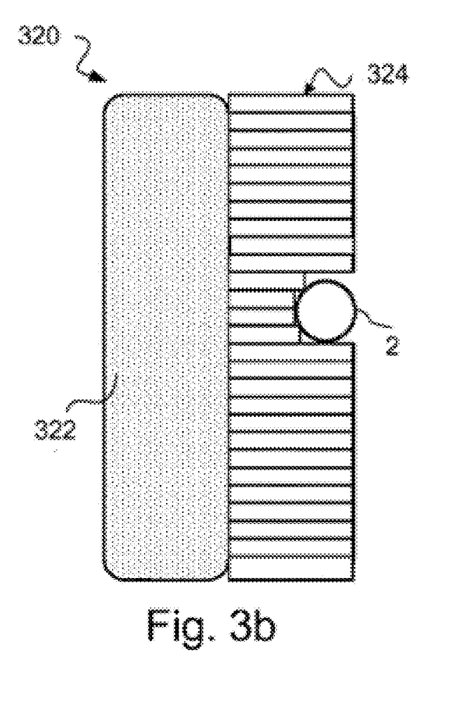

In one embodiment, as seen in FIGS. 3a-b the means for applying pressure 320 comprises two layers; a sound absorbing layer 322 and an adaptive layer 324. Here the adaptive layer 324 comprises actuation means. The actuation means 324 comprises a plurality of cylinders 326a-z.

Once external pressure, such as from a pair of glasses, is applied to one or a plurality of cylinders 326, the one or more cylinders will retract. The cylinders may retract by shortening the length of each cylinder, or by pressing the cylinders down in the underlying sound-absorbing layer 322. Once the external pressure is removed, the cylinders will return back to its original position.

In one embodiment, the thickness of the cylinders arranged in an area where one can expect external pressure (such as from a pair of glasses) are thinner than cylinders arranged in other areas of the earmuff cup assembly 100. The smaller cylinders allows for more cylinders in that expected "problem area", which will further increase the pressure distribution.

In this embodiment a large amount of cylinders are used as actuation means, however it should be noted that the numbers of cylinders 326 are dependent of the size of the cylinders 326 as well as of the size of the earmuff cup assemblies 10. The numbers of cylinders could thus vary between approximately 5 to 100.

The cylinders may be constructed by hydraulic cylinders or retractable springs.

The actuation means may be covered with thin soft layer (not shown) arranged to be adjacent to the user's ear 4 for comfort reasons.

Figure 4:
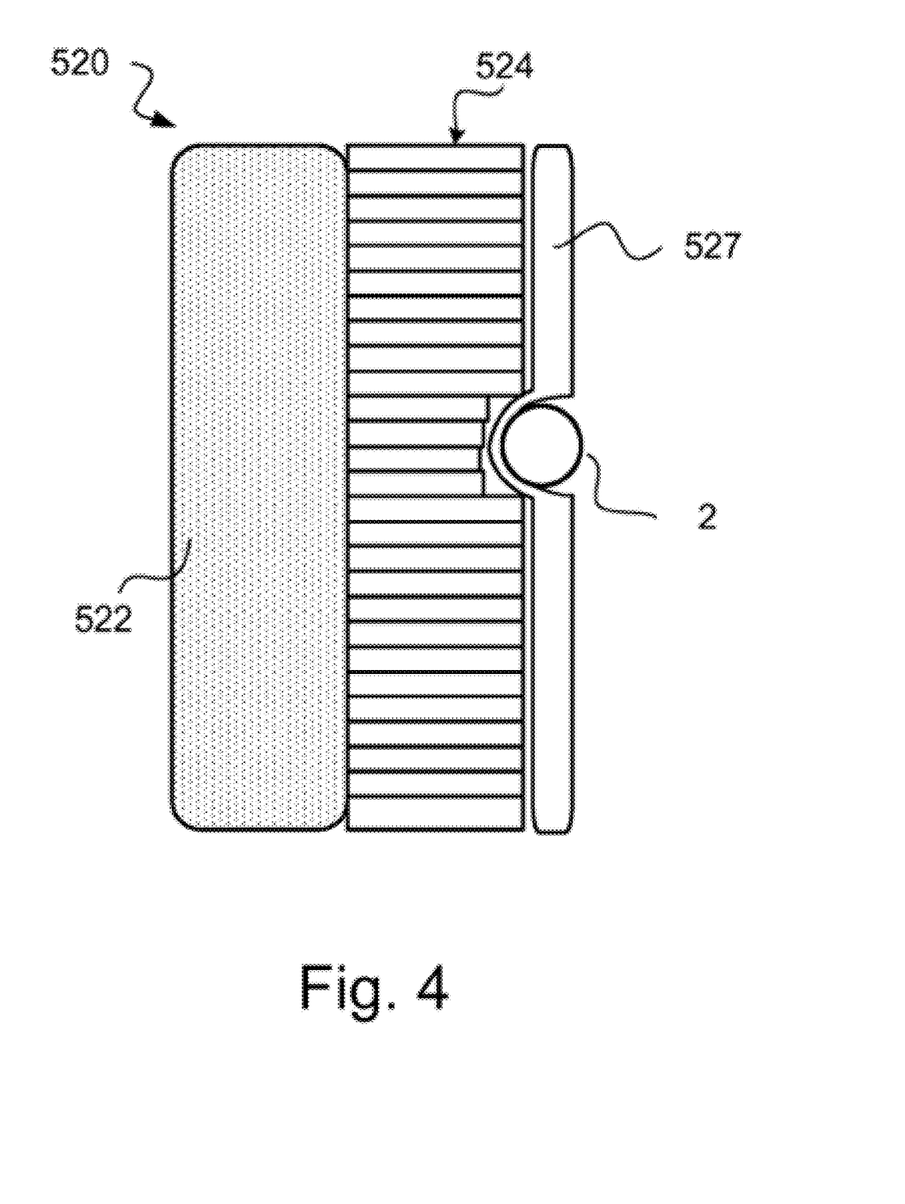
FIG. 4 shows means for applying pressure in an earmuff cup assembly according to one embodiment of the teachings of this application.

Some embodiments may even have more than one sound absorbing layer, and/or more than one adaptive layer for increased comfort and a more evenly distributed pressure. In one embodiment the means for applying pressure 520 comprises two adaptive layers 524, a first layer 556 and a second layer 527, as seen in FIG. 4. Here, the first layer 524 is arranged in between the sound absorbing layer 522 and the second layer 527. The first layer 556 may comprise actuation means as described herein. The second layer 527 may comprise a thin layer of material which distributes the pressure so to increase the efficiency of the actuators in the first layer 556.

In one embodiment the second layer 527 comprise a plurality of small items such as PVC pellets, expanded polystyrene or expanded polypropylene as been described with reference to FIG. 2a-b.

In yet one embodiment the second layer 527 comprises an enclosed liquid, preferably a thick, slow moving viscid liquid. As already mentioned that adaptive layer is relatively thin so as to avoid a drop shaped form of the adaptive layer.

In yet one embodiment the second layer 527 comprises a plurality of high-density foams, wherein at least some of the foams are formed by trapping pockets of gas in a liquid or solid state. The second layer 527 may also comprise a plurality of thin sheets of flexible polyvinyl chloride or polyurethane, where one of the sheets is vacuum formed filled with foam and/or liquid.

Figure 5:
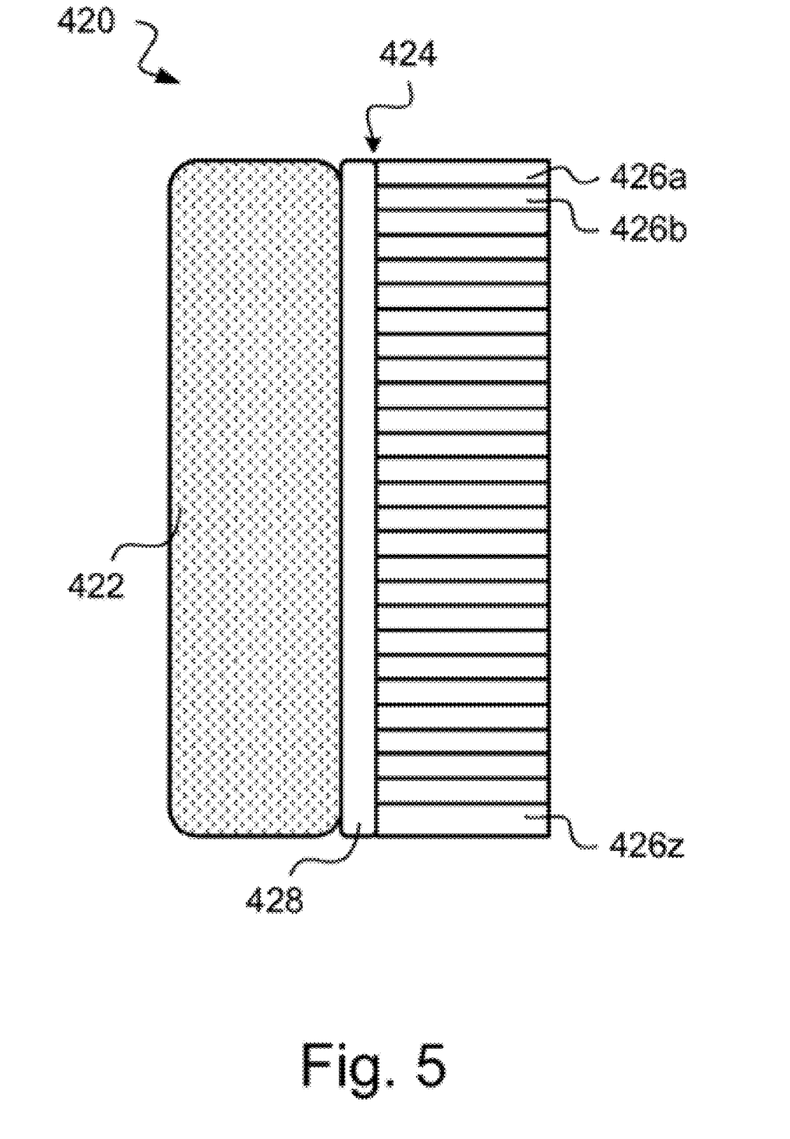
FIG. 5 shows means for applying pressure in an earmuff cup assembly according to one embodiment of the teachings of this application.

FIG. 5 show an embodiment of a means for applying pressure 420 comprising a sound absorbing layer 422 and an adaptive layer 424 comprising means for detecting pressure 428. This will be further described with reference to FIG. 6 which shows a means for applying pressure 420 comprising a sound absorbing layer 422, an adaptive layer 424 and a controller 460. The adaptive layer 424 comprises means for detecting pressure 428. In one embodiment the adaptive layer 424 further comprises a force collector such as actuation means 426. Optionally, the means for applying pressure further comprises a user interface 464 and/or a communication interface 466.

Figure 6:
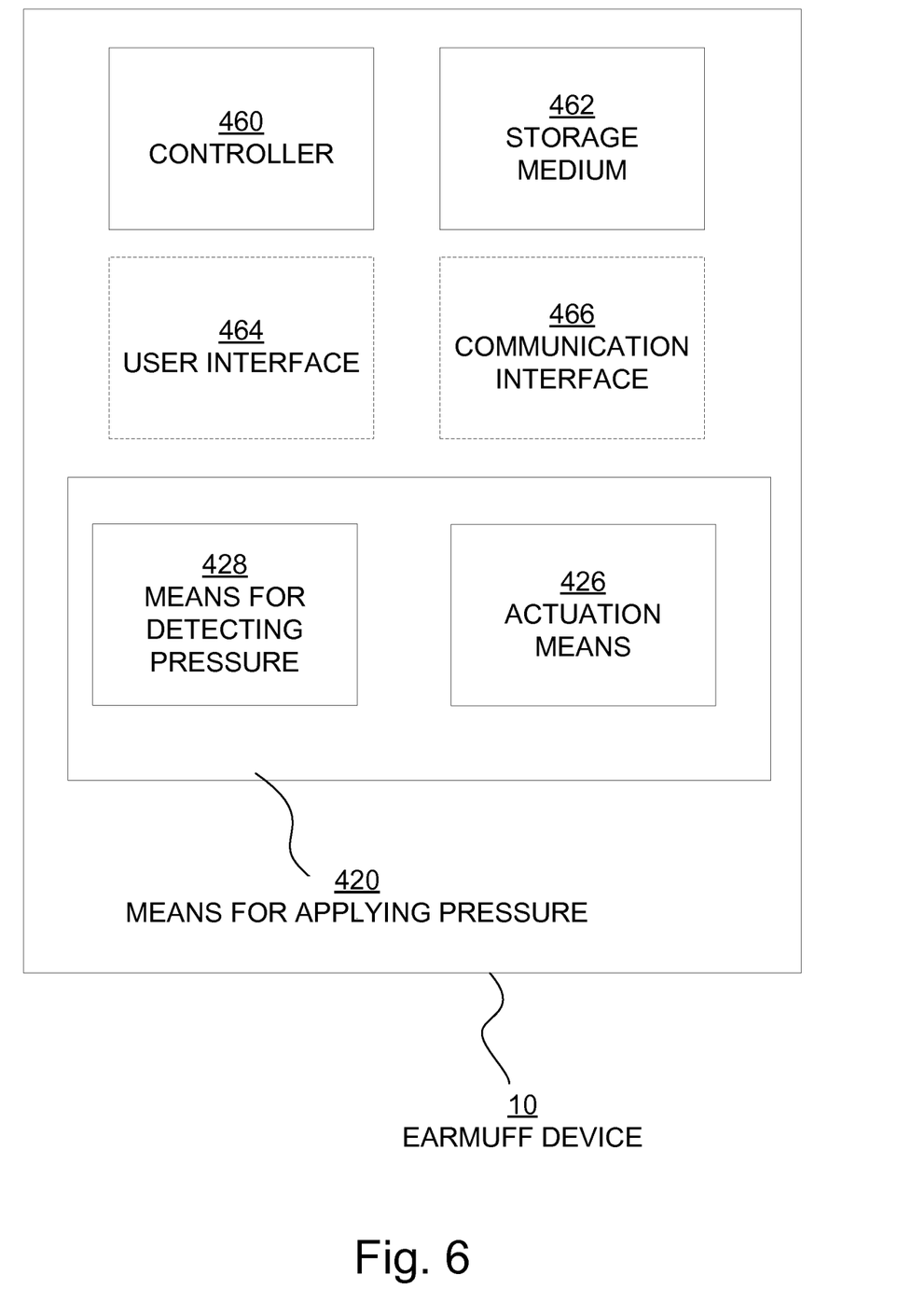
FIG. 6 shows a schematic view of means for applying pressure according to one embodiment of the teachings of this application.

The controller 460 may be implemented using instructions that enable hardware functionality, for example, by using executable computer program instructions in a general-purpose or special-purpose processor that may be stored on a computer readable storage medium (disk, memory etc.) 462 to be executed by such a processor. The controller 460 is configured to read instructions from a memory 462 and execute these instructions to control the pressure. The controller 460 may be implemented using any suitable, publically available processor or Programmable Logic Circuit (PLC). The memory 462 may be implemented using any commonly known technology for computer-readable memories such as ROM, RAM, SRAM, DRAM, FLASH, DDR, SDRAM or some other memory technology.

The controller 460 is connected to the means for detecting pressure 428 and the controller 460 is configured to process any signals received from the means for detecting pressure 428. From the signal received from the means for detecting pressure 428 the controller 460 detects the pressure between the head and the earmuff device 10. Furthermore, the controller 560 is connected to the adaptive layer 424 for controlling the pressure applied to the ear. The controller 460 is configured to determine if an obstacle, such as for example a pair of glasses or hearing aid, is detected, and if so evenly distribute the pressure around the earmuff cup assembly 100.

In one embodiment the controller is configured to receive a detection signal from the means for detecting pressure 428 that an uneven pressure is detected in an area and in response thereto transmit an activation signal to the actuation means so that the cylinders in that area will retract accordingly, thereby reducing the pressure applied by those cylinders and thereby adapting the shape of the adaptive layer locally.

In one embodiment the means for detecting pressure is a pressure sensor 428. The pressure sensor 428 determines the applied pressure around the ear 4 of the user 1 and sends a signal to the controller to tighten the earmuff cup assemblies 100 by applying more pressure to the head of the user 1. The pressure sensor could for example use pressure-sensing technology such as piezoresistive strain gauge, capacitive, electromagnetic, piezoelectric, optical or potentiometric. In one embodiment the pressure sensor is a resistive plate.

The actuation means 424 comprises a plurality of cylinders or pistons. The numbers of cylinders/pistons used are dependent of the size of the cylinders/pistons as well as of the size of the earmuff cup assemblies 10. The actuation means may be covered with thin soft layer (not shown) arranged to be adjacent to the user's ear 4 for comfort reasons.

In one embodiment, the thickness of the cylinders arranged in an area where one can expect external pressure (such as from a pair of glasses 2) are thinner than cylinders arranged in other areas of the earmuff cup assembly 100. The smaller cylinders allows for more cylinders in that expected "problem area", which will further increase the pressure distribution.

Once external pressure, such as from a pair of glasses 2, is detected by the means for detecting pressure 428 a detection signal is sent to the controller 460. The controller 460 will then activate the relevant area in the actuation means 424, i.e. the cylinders/pistons that are arranged in the area where the external pressure is detected. The cylinders/pistons that are activated will thus retract. This causes a decrease in pressure in the relevant area.

In one embodiment the cylinders/pistons retract by shortening the length of each cylinder.

In another embodiment the cylinders/pistons retract by the cylinders/pistons down in the underlying sound-absorbing layer 422.

Once the means for detecting pressure 428 no longer detects an external pressure, a signal is sent to the controller 460 which in turn deactivates the actuation means 424 in at least that area. Once deactivated, the cylinders/pistons will return back to its original position.

In some embodiments, the earmuff device 10 also comprises a user interface 464 for presenting user data to a user 1. The user interface 464 may for example comprise a light indicator, a speaker and/or a screen. The user interface 464 may indicate battery level and/or if both earmuff cup assemblies are correctly arranged on the head of the user.

The user interface 464 may be connected to the controller 460. If the controller 460 detects that the user 1 of the earmuff device 10 is not wearing both earmuff cup assemblies correctly the controller 460 sends a signal to the user interface 464. The user interface 464 may alert the user by a sound, a light indicator and/or by a message on a screen. In one embodiment, the user interface alerts the user by sending out an annoying sound through the earmuff cup assembly 100 that is worn correctly. The alert-sound may also be sent out from both earmuff cup assemblies 100. The user interface 464 may also alert the user by light indicators arranged on the earmuff device 10, for example by sending out a red light or sending out a flashing light.

In some embodiments the earmuff device 10 comprises a communication interface 466, which is adapted to allow the earmuff device 10 to communicate with other devices through the use of different communication technologies. Such communication technologies may be wired or wireless. Examples of such wired technologies are Universal Serial Bus (USB) and Ethernet to name a few. Examples of such wireless technologies are IEEE 802.11, IEEE 802.15, ZigBee, WirelessHART, WIFI, Bluetooth®, W-CDMA/HSPA, GSM, UTRAN and LTE to name a few. It should be noted that other technologies exist and are taken to be an obvious equivalent for such wireless communication interfaces 466.

The earmuff device 10 may be in communication with a power tool comprising a communication interface 466, such as a chainsaw, pole saw, string trimmer, power saw, cut off saw, sander or similar power tools. The communication interface 466 in the earmuff device 10 may receive information relating to the state of the power tool, such as if it is in a working mode or an idle state. In one embodiment, the power tool will only be able to be set into working mode once the acoustic earmuff device 10 sends, via the communication interface, a verification signal that the earmuffs are correctly arranged on the user of the power tool. In this example the power tool will stay in an idle state, for instance powered up but not given enough throttle to do any actual work, until a verification signal from the earmuff device is received.

In one embodiment, the power tool will be switched off and put into idle mode as soon as the power tool no longer receives continual verification signals that the earmuff devices are correctly arranged.

In one embodiment the earmuff device 10 is be considered to be correctly arranged if both earmuff cup assemblies 100 are arranged on the user. In one embodiment the earmuff device 10 is considered to be correctly arranged if at least one of the earmuff cup assemblies 100 are arranged on the user.

In order for the earmuff device 10 to accurately communicate with a power tool they may need to be wirelessly paired. This may be done by the use of an identifier. The identifier is transmitted by either the earmuff device 10 or by the power tool to the other part where it is evaluated. The user may need to verify the connection for example using a pin-code, push a button or the like.

Furthermore, if the earmuff device 10 is used for example by operators felling trees, there may be additional features to alert nearby operators that the current user is in risk of damaging his/hers hearing. The earmuff device 10 may thus comprise a controller 460 and a communication interface 466 which sends out a wireless alert signal to nearby operators if the user is not correctly wearing both earmuff cup assemblies. The alert signal could thus inform the other operators that one user is not correctly wearing its earmuff device 10 and that they should thus stop working for a while. The warning signal may be sent via Bluetooth and may be received by the nearby operators through their ear protections or helmets having a communication interface. The signal could be in the form of an audible signal such as siren, a haptic signal such as a vibration, a visual signal such as a strobe light or other sensory alarm that could be arranged on an operator in the form of a helmet or ear protection.

In one embodiment the earmuff device has a radio frequency alert interface. The radio frequency alert interface is configured to be communicatively connected to an external device, such as an other user's earmuff device. The radio frequency alert interface may be connected to more than one external device, so that alerts may be given to more than one person, thereby increasing the safety in the general area, especially when persons are wearing ear protections. The radio frequency alert interface may be connected directly to the ear protections or through a router. The router may also be connected to a server keeping track of the operators earmuff device status, i.e. if a person is wearing the earmuffs correctly.

Figure 7:
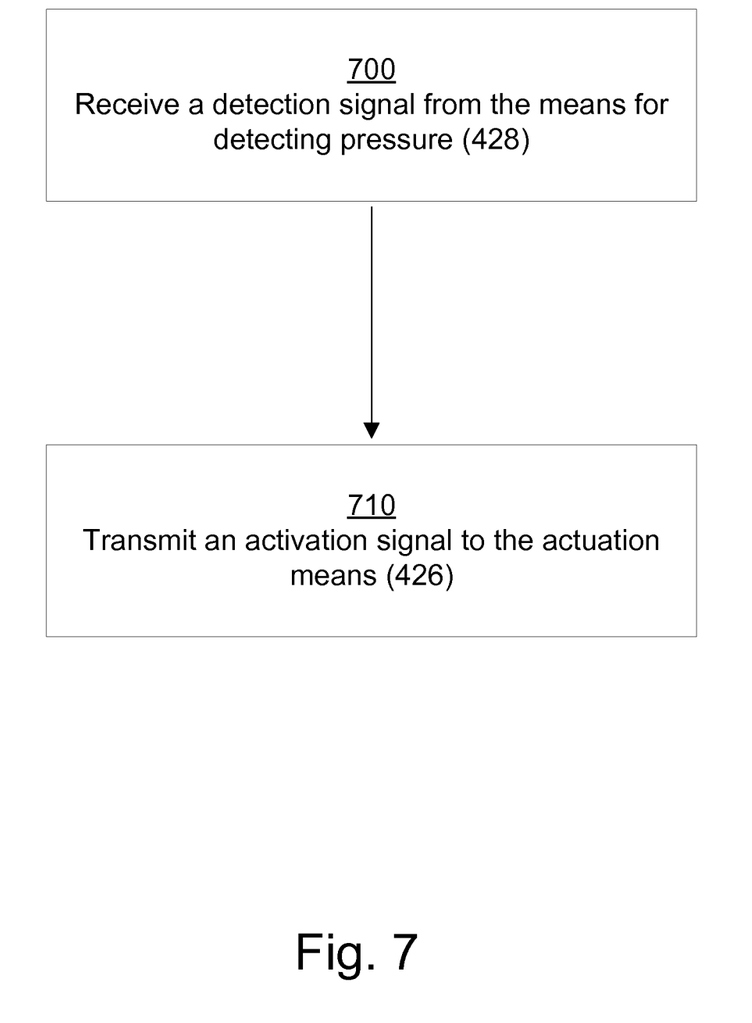
FIG. 7 shows a flowchart representing a method for improved use of an acoustic earmuff device according to one embodiment of the teachings of this application.

A flowchart of a method for improved use of an acoustic earmuff device is shown in FIG. 7. In the embodiment shown, the acoustic earmuff device 10 comprises a controller 460 and an adaptive layer 424. The adaptive layer 424 comprises actuation means 426 and means for detecting pressure 428. The method comprises adaptation of the means for applying pressure 120; 220; 320; 420; 520 so that the pressure around the ear is evenly distributed and an even seal is thereby achieved. A detection signal is received 700 from the means for detecting pressure 428 comprising information that an uneven pressure is detected in an area. In a next step an activation signal is transmitted 710 to the actuation means so that the cylinders in that area will retract.

The invention has mainly been described above with reference to a few embodiments. However, as is readily appreciated by a person skilled in the art, other embodiments than the ones disclosed above are equally possible within the scope of the invention, as defined by the appended patent claims.

The invention claimed is:

1. An acoustic earmuff device comprising:
    a pair of earmuff cup assemblies, wherein each earmuff cup assembly of the pair of the pair of earmuff cup assemblies is configured to be arranged at a location proximate to an ear of a user; and
    a controller configured to detect if the user is wearing both earmuff cup assemblies, and if not send a signal to a communication interface of the acoustic earmuff device, the communication interface being configured to, in response to the signal, wirelessly transmit a deactivation signal to a power tool to put the power tool into idle mode;
    wherein, in the idle mode, the power tool is powered but the throttle is prevented from activating the power tool to perform actual work;
    wherein the controller is further configured to wireless transmits a verification signal to the power to cause the power tool to transition to a working mode that permits the throttle to activate the power tool to perform actual work in response to the controller detecting that both of the earmuffs cup assemblies are being worn by the user.

2. The acoustic earmuff device according to claim 1, wherein each earmuff cup assembly comprises means for adapting a pressure applied to the location proximate to the ear so that the pressure around the ear is evenly distributed and an even seal is achieved, wherein the means for adapting the pressure comprises an adaptive layer that is configured to apply the pressure around the ear evenly regardless of whether the location proximate to the ear comprises a protruding element, accommodating for the protruding element.

3. The acoustic earmuff device according to claim 2, wherein the means for adapting pressure further comprises a sound-absorbing layer comprising a sound-absorbing material;
wherein the sound-absorbing layer is arranged adjacent to the adaptive layer, and wherein the adaptive layer is arranged proximate the ear of the user when in use.

4. The acoustic earmuff device according to claim 2, wherein the adaptive layer comprises a plurality of small items which are free to move around in the adaptive layer as a local pressure is being applied to the adaptive layer so that the adaptive layer adapts a shape of the adaptive layer depending on the location proximate to the ear.

5. The acoustic earmuff device according to claim 2, wherein the adaptive layer comprises a liquid.

6. The acoustic earmuff device according to claim 2, wherein the adaptive layer comprises actuation means.

7. The acoustic earmuff device according to claim 6, wherein the actuation means comprises a plurality of cylinders which are configured to retract if the pressure is unevenly distributed in the location proximate to the ear.

8. The acoustic earmuff device according to claim 7, wherein the adaptive layer comprises actuation means and means for detecting pressure, and said controller is configured to:
    receive a detection signal from the means for detecting pressure that an uneven pressure is detected in an area and
    transmit an activation signal to the actuation means so that the cylinders in that area will retract.

9. The acoustic earmuff device according to claim 8, wherein the means for detecting pressure is a pressure sensor.

10. The acoustic earmuff device according to claim 2, wherein the sound absorbing layer and the adaptive layer are one and the same layer.

11. An acoustic earmuff device comprising:
    a pair of earmuff cup assemblies such that each earmuff cup assembly is configured to be arranged at a location proximate to an ear of a user;
    wherein each earmuff cup assembly comprises means for adapting a pressure applied to the location proximate to the ear so that the pressure around the ear is evenly distributed and an even seal is achieved;
    wherein the means for adapting the pressure comprises an adaptive layer that is configured to apply the pressure around the ear evenly regardless of whether the location proximate to the ear comprises a protruding element, accommodating for the protruding element;
    wherein the means for adapting pressure further comprises a sound-absorbing layer comprising a sound-absorbing material;
    wherein the sound-absorbing layer is arranged adjacent to the adaptive layer, and wherein the adaptive layer is arranged proximate the ear of the user when in use.

12. The acoustic earmuff device according to claim 11, wherein the adaptive layer comprises at least one of
    a plurality of small items which are free to move around in the adaptive layer as a local pressure is being applied to the adaptive layer so that the adaptive layer adapts a shape of the adaptive layer depending on the location proximate to the ear;
    a liquid; and
    actuation means.

13. The acoustic earmuff device according to claim 11, wherein the acoustic earmuff device further comprises a controller and where the adaptive layer comprises an actuator and a pressure detecting arrangement, wherein said controller is configured to:

receive a detection signal from the pressure detecting arrangement that an uneven pressure is detected in an area; and in response to the detection signal, transmit an activation signal to the actuator.

14. An acoustic earmuff device comprising:

a pair of earmuff cup assemblies, wherein each earmuff cup assembly of the pair of the pair of earmuff cup assemblies is configured to be arranged at a location proximate to an ear of a user;

a controller configured to:

detect both earmuff cup assemblies are positioned at the location proximate to an ear of a user;

in response to detecting both earmuff cup assemblies are positioned at the location proximate to an ear of a user, continually transmit wireless verification signals to a power tool to maintain the power tool to be in a working mode that permits a throttle of the power tool to activate the power tool to perform actual work;

detect both earmuff cup assemblies are not positioned at the location proximate to an ear of a user; and in response to detecting both earmuff cup assemblies are not positioned at the location proximate to an ear of a user, discontinue transmission of the wireless verification signals to the power tool to cause the power tool to transition into an idle mode that prevents the throttle from activating the power tool to perform actual work.

* * * * *